(12) United States Patent
Muto et al.

(10) Patent No.: US 9,044,290 B2
(45) Date of Patent: Jun. 2, 2015

(54) JOINT BETWEEN MOTOR UNIT AND POWER CORDS OF DENTAL HANDPIECE

(75) Inventors: Shinichirou Muto, Kanuma (JP); Atsushi Okada, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 12/868,887

(22) Filed: Aug. 26, 2010

(65) Prior Publication Data
US 2011/0053409 A1    Mar. 3, 2011

(30) Foreign Application Priority Data

Aug. 27, 2009 (JP) .................................. 2009-196517

(51) Int. Cl.
*H01R 13/52* (2006.01)
*A61C 1/06* (2006.01)
*A61C 1/08* (2006.01)

(52) U.S. Cl.
CPC .. *A61C 1/06* (2013.01); *A61C 1/088* (2013.01)

(58) Field of Classification Search
USPC ................................................ 439/281, 320
See application file for complete search history.

(56) References Cited

U.S. PATENT DOCUMENTS

| | | | | |
|---|---|---|---|---|
| 2,103,548 | A * | 12/1937 | Obermaier | 439/741 |
| 3,789,346 | A * | 1/1974 | De Brick | 439/283 |
| 4,808,127 | A * | 2/1989 | Swanic | 439/139 |
| 5,368,499 | A * | 11/1994 | Hirt | 439/350 |
| 5,401,181 | A * | 3/1995 | Wilson | 439/281 |
| 5,649,835 | A * | 7/1997 | Weed | 439/320 |
| 7,785,123 | B2 * | 8/2010 | Corona | 439/281 |
| 2009/0160271 | A1 | 6/2009 | Bischof et al. | |

FOREIGN PATENT DOCUMENTS

| | | |
|---|---|---|
| EP | 0 727 190 A1 | 8/1996 |
| EP | 0 745 358 A1 | 12/1996 |
| JP | 1980087177 U | 6/1980 |
| JP | 2001 029361 A | 2/2001 |
| JP | 2003 116889 A | 4/2003 |
| JP | 2009148569 A | 7/2009 |
| WO | 2006/002692 A1 | 1/2006 |
| WO | 2007/143071 A2 | 12/2007 |

* cited by examiner

*Primary Examiner* — Tho D Ta
(74) *Attorney, Agent, or Firm* — Jason D. Voight

(57) ABSTRACT

The joint of the present invention facilitates connection and disconnection of the motor unit to and from the power cords in the hose, and makes the connecting area between these two parts as compact as practicable. In the joint, the motor-unit-side connector is arranged projecting from the connecting-end opening of the motor casing 10, whereas the power-cord-side connector is arranged offset from the connecting-end opening of the end cap 20, so that the two connectors are connectable inside the end cap 20.

10 Claims, 6 Drawing Sheets

JOINT BETWEEN MOTOR UNIT AND POWER CORDS OF DENTAL HANDPIECE

FIELD OF ART

The present invention relates to a joint between a motor unit and power cords therefor of a dental handpiece.

BACKGROUND ART

A dental handpiece generally has a grip section mainly composed of, as shown in FIGS. 6 and 7, generally cylindrical motor casing 90, motor unit 91 detachably accommodated in the motor casing 90 and supplying driving force to a dental tool, generally cylindrical end cap 92 connected to hose 93 which accommodates power cords for supplying power to the motor unit 91, and detachably connectable to the proximal end of the motor casing 90 and, and motor-unit-side connector 94 and power-cord-side connector 95 arranged between the motor casing 90 and the end cap 92 for electrically connecting the motor unit 91 and the power cords in the hose 93. The motor-unit-side connector 94 includes a plurality of pins 941, which are connected to the motor unit 91 and arranged in parallel in the opening of the motor casing 90 at its end to be connected to the end cap 92 as shown in FIG. 8. The power-cord-side connector 95 includes a plurality of sockets 950 for connectively receiving the pins 941 on the motor unit side. The sockets 950 are arranged slightly projecting outwards from the opening of the end cap 92 at its end to be connected to the motor casing 90. By connecting the motor casing 90 to the end cap 92 as shown in FIG. 9, the motor unit 91 and the power cords in the hose 93 are electrically connected. The end cap 92 has a distal end having a larger diameter which is the same as the diameter of the proximal end of the motor casing 90, and a proximal end having a smaller diameter and capable of receiving the hose 93 therein, and has a contour tapered from the distal to proximal end. The smaller diameter part in the proximal end portion functions as a sensor detectable part, at which an instrument hanger of a dental unit detects whether the motor is in use or not.

In this way, the grip section of a dental handpiece is composed of five parts, namely the motor casing 90, motor unit 91, connectors 94, 95, and end cap 92 (sensor detectable part). The motor-unit-side connector 94, specifically the pins 941, is arranged in the connecting-end opening of the motor casing 90, while the power-cord-side connector 95, specifically the sockets 950, is arranged slightly projecting outwards from the connecting-end opening of the end cap 92, so that the connectors 94 and 95 are connected in the connecting-end opening of the motor casing 90. Due to this structure, the connecting area between the motor unit 91 and the power cords in the hose 93 becomes long, which increases the length and weight of the overall grip section. Such a long, heavy handpiece imposes a work burden on dentists and dental technicians, who use a handpiece all day long.

In order to overcome this drawback, there is proposed a light and compact dental handpiece for reducing the work burden on dentists and dental technicians even their work lasts for a prolonged period of time. Patent Publication 1 discloses an example of such a dental handpiece, wherein motor M is connected to hose C (flexible tube) without a separate coupling. In this handpiece, by direct connection, the connecting area between the motor M and the hose C is minimized, which remarkably reduces the overall length and weight of the handpiece, especially of the grip section.
Patent Publication 1: JP-2009-148569 (see paragraph 0005 and FIG. 1)

However, in dental treatment, tools are usually sterilized after each treatment in order to prevent in-hospital infection of various pathogens between patients, and the motor is detached from the hose and subjected to autoclaving and the like treatment. With the above-mentioned conventional dental handpiece wherein the motor and the hose are directly connected, detachment of the motor is complicated, which lowers work efficiency. This problem is also discussed in paragraph 0005 of patent Publication 1.

SUMMARY OF THE INVENTION

The present invention aims to solve these drawbacks of the prior art. It is an object of the present invention to provide a joint between a motor unit and power cords therefor of a dental handpiece of this type which facilitates connection and disconnection of the motor unit to and from the hose (power cords), which makes the connecting area between these two members as compact as practicable to thereby remarkably reduce the length and weight of the grip section of a dental handpiece, and in turn makes the overall dental handpiece compact and light.

According to the present invention, there is provided a joint for connecting a motor unit to a power cord of a dental handpiece, comprising:
a generally cylindrical motor casing,
a motor unit detachably accommodated in said motor casing and supplying driving force to a dental tool,
a generally cylindrical end cap connected to a hose which accommodates a power cord for supplying power to the motor unit, and detachably connectable to one end of the motor casing and, and
a motor-unit-side connector and a power-cord-side connector arranged between the motor casing and the end cap for mutual electrical engagement,
said motor casing having an opening at its end to be connected to said end cap,
said end cap having an opening at its end to be connected to said motor casing,
connection of the motor casing to the end cap causing said motor unit to be electrically connected to the power cord,
wherein said motor-unit-side connector is arranged projecting outwards from the opening of the motor casing, and said power-cord-side connector is arranged offset from the opening of said end cap into an interior of the end cap, and
wherein said motor-unit-side connector is connectable to said power-cord-side connector inside the end cap.

In preferred embodiments, the joint may have the following structures.

(1) A guiding projection and a guiding recess capable of receiving the guiding projection therein are provided for guiding connection of the motor-unit-side connector to the power-cord-side connector, wherein the guiding projection is provided either in the opening of the motor casing or inside the end cap, and the guiding recess is provided in the other.

(2) In a joint having the structure mentioned in (1) above, the guiding projection is a guide pin projecting from the opening of the motor casing or inside the end cap in the direction of connection of the motor-unit-side and power-cord-side connectors outwardly beyond the motor-unit-side or power-cord-side connector, and the guiding recess is a guide pit extending inside the end cap or from the opening of the motor casing in the direction of connection of the motor-unit-side and power-cord-side connectors, so that the guide pin is insertable into the guide pit.

(3) One of the motor-unit-side connector and the power-cord-side connector includes a pin which is connected to the motor unit or the power cord and arranged in the opening of the motor casing or inside the end cap in the direction of connection of the motor-unit-side and power-cord-side connectors, and the other of the motor-unit-side connector and the power-cord-side connector includes a socket for receiving the pin therein, which socket is connected to the power cord or the motor unit and arranged inside the end cap or in the opening of the motor casing in the direction of connection of the motor-unit-side and power-cord-side connectors.

(4) The power cord along with at least one of a fluid tube for conveying fluid and a power cord for supplying power to a light source extend through the hose; the motor unit along with at least one of a pipe for conveying the fluid and wiring for supplying the power to the light source are accommodated in the motor casing; the motor-unit-side connector along with at least one of an end of the pipe and a power terminal/socket connected to the wiring are projected from the opening of the motor casing in parallel with each other; and the power-cord-side connector along with at least one of a pipe socket and a power socket/terminal connected to the pipe for conveying the fluid or the power terminal/socket are arranged offset from the opening of the end cap into the interior of the end cap in parallel with each other.

(5) In a joint having the structure mentioned in (4) above, the motor-unit-side connector and at least one of the end of the pipe and the power terminal/socket are arranged in circle near and around the center of the opening of the motor casing in parallel with each other, and the power-cord-side connect or and at least one of the pipe socket and the power socket/terminal are arranged in circle near and around the center of the end cap in parallel with each other.

(6) A step protruding from the opening of the motor casing is formed, which step has a smaller diameter sized so that the opening of the end cap is capable of fitting thereon.

(7) In a joint having the structure mentioned in (6) above, the step of the motor casing has male thread formed on its outer circumference, and the end cap has female thread formed circumferentially on its inner surface near the opening, so that the motor casing is capable of being screwed and fixed to the end cap.

(8) A protect ion cap detachably attachable to the motor casing in place of the end cap is provided for covering the opening of the motor casing to protect the motor-unit-side connector when the end cap is not on the motor casing.

In the joint for connecting a motor unit to a power cord of a dental handpiece according to the present invention, which has the above structure, the motor-unit-side connector is arranged projecting outwards from the opening of the motor casing, whereas the power-cord-side connector is arranged offset from the opening of the end cap into the interior of the end cap, and the two connectors are connectable inside the end cap. Thus, connection and disconnection of the motor unit to and from the hose is facilitated, the connecting area between these two members is made as compact as practicable to thereby remarkably reduce the length and weight of the grip section of a dental handpiece, and the overall dental handpiece is made compact and light. Further, since the power-cord-side connector is offset from the opening of the end cap into the interior of the end cap, the connector is hard to be touched by the user. Thus, even when the motor unit is detached from the end cap while the connector in the end cap is energized, the risk of the user to accidentally touch the connector is eliminated or at least significantly reduced, to thereby improve safety.

PREFERRED EMBODIMENTS OF THE INVENTION

The present invention will now be explained in detail with reference to the attached drawings.

Figure 1:
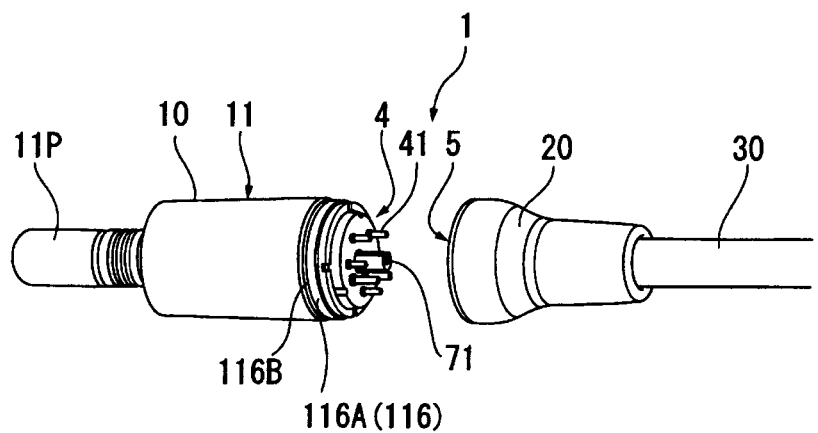
FIG. 1 is a perspective view of an embodiment of the joint between a motor unit and power cords therefor of a dental handpiece according the present invention in a detached state.
Figure 2:
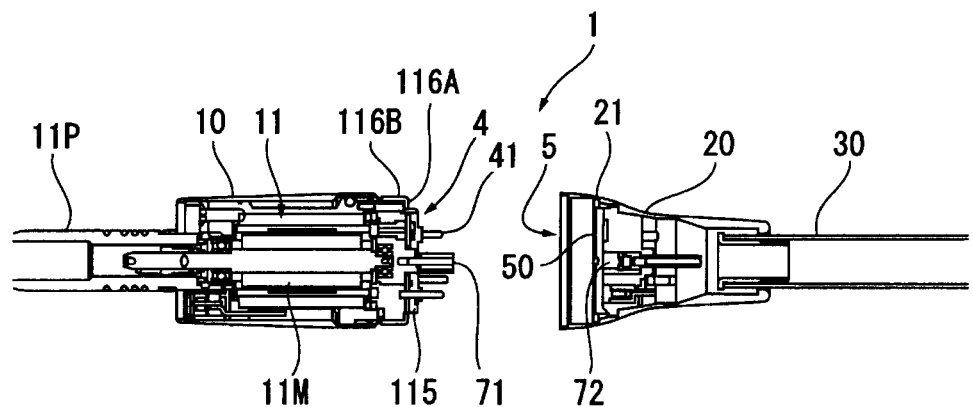
FIG. 2 is a longitudinal sectional view of the joint of FIG. 1.

FIGS. 1 to 5 show a joint between a motor unit and power cords therefor of a dental handpiece. Referring to FIGS. 1 and 2, joint 1 includes a generally cylindrical motor casing 10, a motor unit 11 axially detachably accommodated in the motor casing 10 and supplying driving force to a dental tool (not shown), a generally cylindrical end cap 20 connected to hose 30 which accommodates power cords for supplying power to the motor unit 11, and detachably connectable to the proximal end of the motor casing 10, and motor-unit-side connector 4 and power-cord-side connector 5 arranged between the motor casing 10 and the end cap 20 for mutual electrical engagement.

Figure 3:
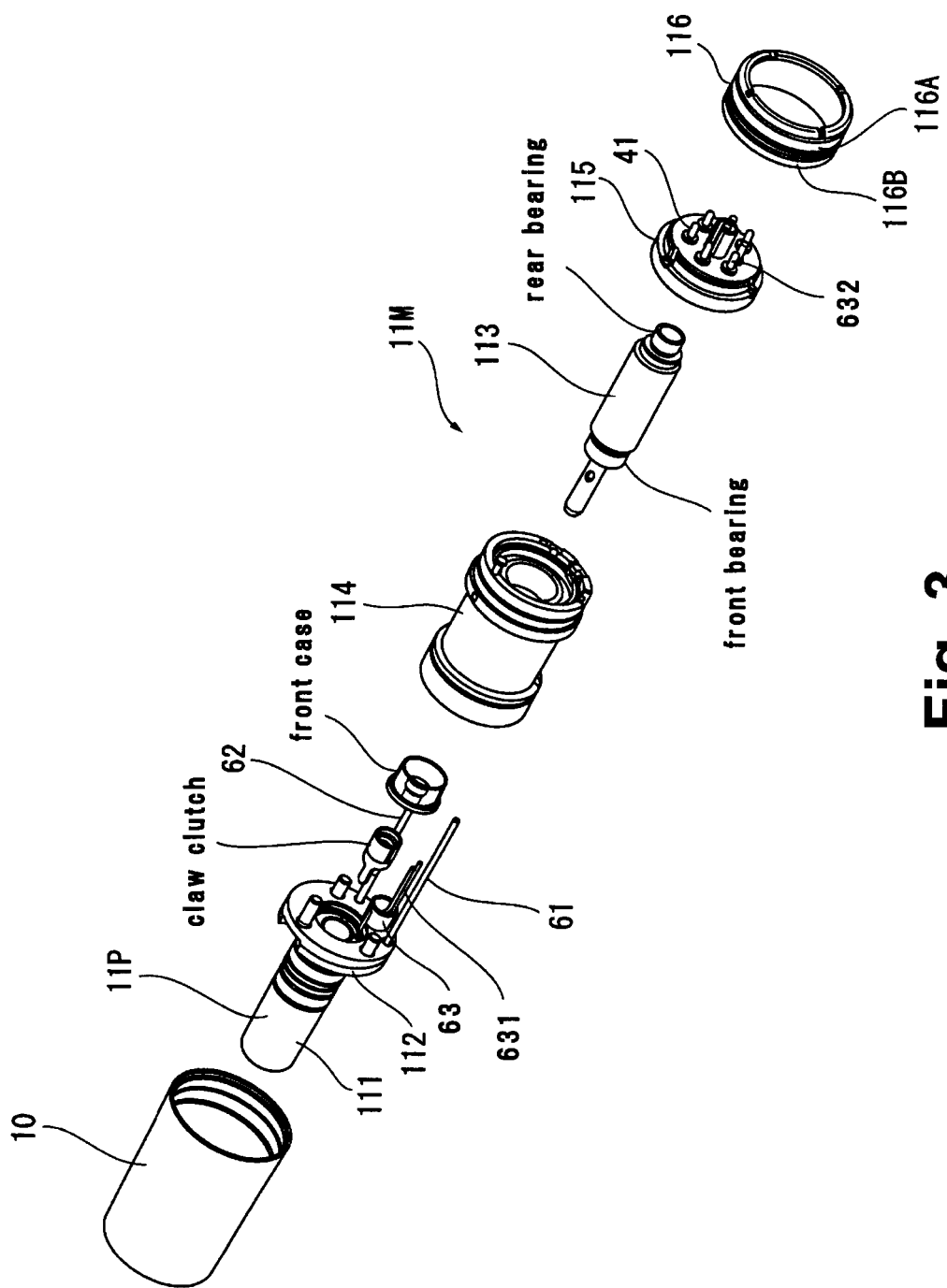
FIG. 3 is an exploded perspective view showing the components of the motor unit.

The motor unit 11 is mainly composed of insert member 11P and motor body 11M, and accommodated in the motor casing 10. As shown in FIG. 3, the insert member 11P includes cylindrical insert 111 to be inserted into a corresponding receptacle in a neck section (not shown) of a handpiece for connection of the grip section to the neck section, and cap 112 provided at one end of the insert 111 and fixed to the distal end of the motor body 11M. The cap 112 has through holes or openings. The motor body 11M is mainly composed of rotor unit 113 and coil/core unit 114. The coil/core unit 114 is provided with through holes or channels corresponding to the through holes or openings of the cap 112. On the distal end of the motor body 11M, the insert member 11P is fixed, whereas on the proximal end of the motor body 11M, pin holder 115 having a plurality of pin holes is fixed, around which threaded ring 116 having the threaded outer surface is fitted to be arranged contiguous to the proximal end of the motor casing 10. The threaded ring 116 has an outer diameter which is generally the same as the inner diameter and smaller than the outer diameter of the motor casing 10, so that the threaded ring 116 forms step 116A protruding from the connecting-end opening of the motor casing 10, onto which step the connecting-end opening of the end cap 20 is to be fitted. The outer surface of the threaded ring 116 functions as male thread 116B, onto which the end cap 20 is capable of being screwed for fixing the motor casing 10 to the end cap 20. The male thread 116B is not necessarily formed over the entire outer surface of the threaded ring 116, but is formed in the distal part of the outer surface. The cap 112 of the insert member 11P and the coil/core unit 114 have through holes or openings, in which various parts are detachably held, such as hollow pin-shaped water pipe 61 and air pipe 62 for transferring water and air (fluid), respectively, to be used in the oral cavity of a patient, light source 63 composed of an LED, and wiring 631 and power terminal (or power socket) 632 for supplying power to the light source 63. The water and air pipes 61 and 62 are inserted into and placed in the through holes of the cap 112 and the coil/core unit 114. The light source 63 is positioned facing to an opening of the cap 112 with its wiring 631 running through a through hole of the coil/core unit 114. The motor unit 11 thus assembled is accommodated in the motor casing 10, with the insert 111 projecting from the distal end of the motor casing 10, the threaded ring 116 contiguous to the proximal end of the motor casing 10, and the pin holder 115 exposed in the connecting-end opening of the motor casing 10. Through the pin holder 115, the motor-unit-side connector 4, one end of the water and air pipes 61 and 62, and the power terminal (or power socket) 632 for the light source 63 are arranged.

The end cap 20 has the distal end having a larger outer diameter which is the same as the outer diameter of the proximal end of the motor casing 10, and the proximal end having smaller outer and inner diameter and receiving the hose 30 therein, and has a contour tapered from the distal to proximal end. The end cap 20 has, at its distal end, a connecting-end opening, which has a diameter sized to be capable of fitting over the step 116A (threaded ring 116) protruding from the connect ing-end opening of the motor casing 10, and on the inner surface near the connecting-end opening, female thread 21 capable of being screwed onto the male thread 116B (threaded ring 116) formed in the outer surface of the step 116A, so that the end cap 20 may be screwed and integrally fixed to the proximal end of the motor casing 10. The proximal end portion of smaller diameter is also a sensor detectable part, at which an instrument hanger of a dental unit detects whether the motor body 11M is in use or not. The hose 30 is inserted into and fixed in the proximal end opening of the end cap 20. Through the hose 30 extend not only the power cords for the motor body 11M, but also a water tube and an air tube for conveying water and air (fluid), respectively, and power codes for supplying power to the light source.

In the joint 1 between the motor unit and the power cords, the motor-unit-side connector 4 is projected from the connecting-end opening of the motor casing 10, whereas the power-cord-side connector 5 is arranged offset from the connecting-end opening of the end cap 20 into the interior of the end cap 20, so that the motor-unit-side connector 4 and the power-cord-side connector 5 are connectable to each other inside the end cap 20. For guiding connection between the connectors 4 and 5, guiding projection 71 projecting from the connecting-end opening of the motor casing 10 and guiding recess 72 recessed inside the end cap 20 for engagement by the guiding projection 71 are formed.

The motor-unit-side connector 4 is composed of pins 41, which are inserted in and held by the pin holder 115 disposed in the connecting-end opening of the motor casing 10, extend in the direction of connection between the connectors 4 and 5 (the direction of connection between the motor casing 10 and the end cap 20), and are connected to the motor unit 11. The power-cord-side connector 5 is composed of sockets 50 for receiving the pins 41 therein. The sockets 50 extend in the end cap 20 in the direction of connection between the connectors 4 and 5 (the direction of connection between the motor casing 10 and the end cap 20), and are connected to the power cords for the motor extending through the hose 30. The guiding projection 71 is in the form of a guide pin, which extends from the connecting-end opening of the motor casing 10 in the direction of connection between the connectors 4 and 5 outwardly beyond the connectors 4. Corresponding to the guiding projection 71, the guiding recess 72 is in the form of a guide pit, which extends in the end cap 2 so as to receive the guide pin 71 therein in the direction of connection between the connectors 4 and 5.

Figure 4:
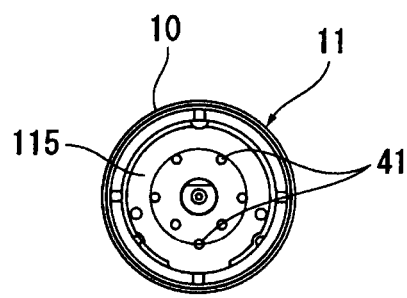
FIG. 4 is a proximal end view of the motor unit showing the arrangement of the motor-unit-side connector and various parts.

As shown in FIG. 4, on the side of the motor unit 11, the pins 41, along with the ends of the water pipe 61 and air pipe 62, and the power terminal 632, are projected from the pin holder 115 disposed in the connecting-end opening of the motor casing 10, and arranged in circle near and around the center of the connecting-end opening in parallel with each other. Corresponding to these parts, on the side of the power cords, the sockets 50, along with a water pipe socket, an air pipe socket, and power socket (these three not shown), are offset from the connecting-end opening of the end cap 20 into the interior of the end cap 20, and arranged in circle near and around the center of the connecting-end opening in parallel with each other. The guiding projection 71 is projected in the center of the connecting-end opening of the motor casing 10 outwardly beyond the pins 41, the ends of the water pipe 61 and the air pipe 62, and the power terminal 632. Correspondingly, the guiding recess 72 is arranged in the center of the connect ing-end opening of the end cap 20, i.e., in the center among the sockets 50, the water and air pipe sockets, and the power socket for the light source.

Figure 5:
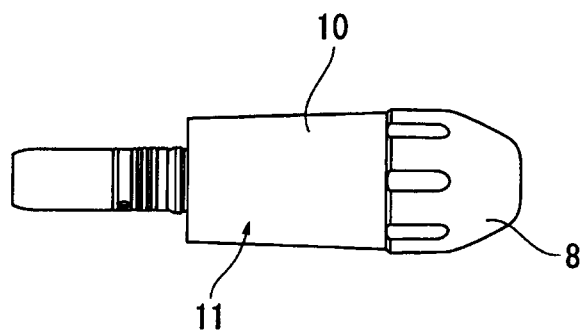
FIG. 5 is a side view of a protective cap attached to the motor casing.
Figure 6:
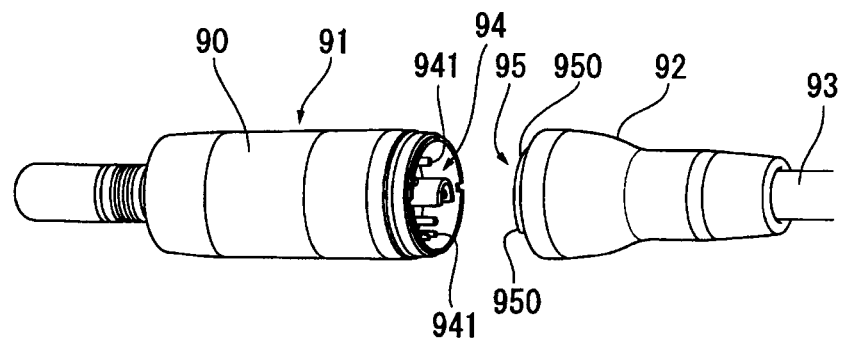
FIG. 6 is a perspective view of a conventional joint between a motor unit and power cords therefor of a dental handpiece in a detached state.
Figure 7:
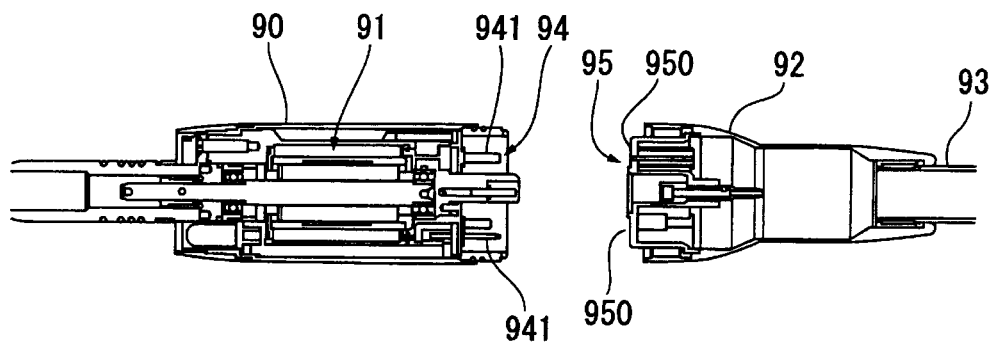
FIG. 7 is a longitudinal sectional view of the joint of FIG. 6.
Figure 8:
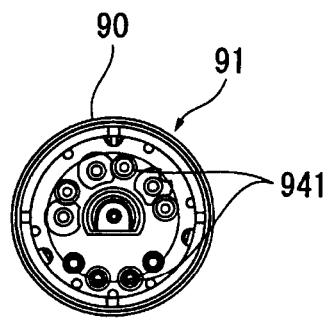
FIG. 8 is a proximal end view of the motor unit of FIG. 6 showing the arrangement of the motor-unit-side connector and various parts.
Figure 9:
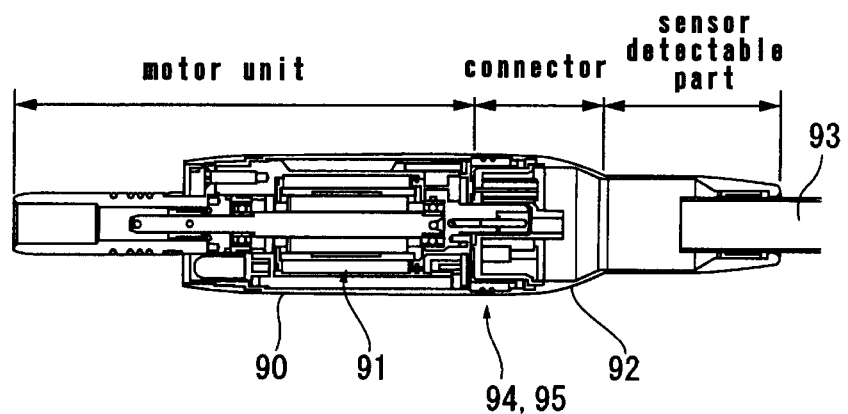
FIG. 9 is a longitudinal sectional view showing the joint of FIG. 6 connecting the motor unit to the power cords.
Figure 10:
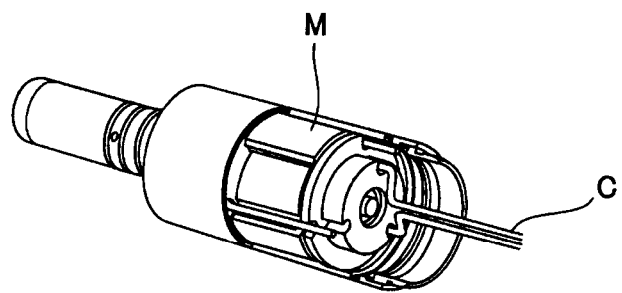
FIG. 10 is a perspective view of another type of a conventional joint between a motor unit and power cords therefor of a dental handpiece.

FIG. 5 shows a protection cap to be used with the motor casing 10. As shown in FIG. 5, protection cap 8, which is made of a hard plastic or a metal material, is generally in the form of a cylinder having an open distal end and a closed proximal end. The protection cap 8 has a larger diameter at its distal end, which is the same as the outer diameter of the proximal end of the motor casing 10, and is tapered toward its proximal end, which is closed with a plane. The opening at the distal end is a connecting-end opening which has a diameter sized to be capable of fitting over the step 116A (threaded ring 116) protruding from the connecting-end opening of the motor casing 10. The protection cap 8 has, on the inner surface near the connecting-end opening, female thread capable of being screwed onto the male thread 116B (threaded ring 116) formed in the outer surface of the step 116A, so that the protection cap 8 may be screwed onto and integrally fixed to the proximal end of the motor casing 10. In this way, after the end cap 20 is detached from the motor casing 10, the protection cap 8 may be detachably attached to the motor casing 10 to cover the connecting-end opening thereof for protecting the connector 4 and the various parts 61, 62, 632 projecting from the connecting-end opening.

In the joint 1 between the motor unit and the power cords, as shown in FIG. 2, by connecting the motor casing 10 and the end cap 20, the motor-unit-side connector 4 is electrically connected to the power-cord-side connector 5 inside the end cap 20, and at the same time, the ends of the water and air pipes 61 and 62, and the power terminal 632 are connected to the corresponding water and air pipe sockets and the power socket for the light source. Here, by aligning the guide pin 71 projecting in the center of the connecting-end opening of the motor casing 10 with the guide pit 72 extending in the center of the connecting-end opening of the end cap 20 and inserting therein, the proximal, connecting end of the motor unit 11 is fit in the end cap 20 through the connecting-end opening of the cap 20, and the pins 41, the ends of the water and air pipes 61 and 62, and the power terminal 632 projecting from the connecting-end opening of the motor casing 10 are connected, inside the end cap 20, to the corresponding sockets 50, water and air pipe sockets, and power socket for the light source offset in the end cap 20. In this state, the threaded ring 116 at the proximal end of the motor casing 10 engages with the female thread 21 on the inner surface of the end cap 20 near the connecting-end opening, and, by rotating the motor casing 10 in the direction for fastening the threaded ring 116, the threaded ring 116 of the motor casing 10 is fastened into the thread 21 of the end cap 20 so that the two members are integrally joined. For detaching the motor unit 11 from the end cap 20, the above procedures are followed in reverse. In this way, the proximal end face of the motor unit 11 is positioned significantly closer to the hose 30 compared to the conventional joint, so that the connecting area between these two members is made much more compact than in the conventional joint.

As discussed above, in the joint 1 between the motor unit and the power cords according to the present invention, the motor-unit-side connector 4, in this embodiment the pins 41, are connected to the motor unit 11 and projected from the connecting-end opening of the motor casing 10 in the direction of connection between the connectors 4 and 5 (the direction of connection between the motor casing 10 and the end cap 20), whereas the power-cord-side connector 5, in this embodiment the sockets 50, are connected to the power cords 31 for motor, offset from the connecting-end opening of the end cap 20 into the interior of the end cap 20, and arranged in the direction of connection between the connectors 4 and 5 (the direction of connection between the motor casing 10 and the end cap 20), so that the connectors 4 and 5 are connectable inside the end cap 20. Thus the connection and disconnection of the motor unit 11 to and from the power cords in the hose 30 are facilitated, the connecting area between the motor unit 11 and the power cords is made as compact as practicable to thereby remarkably reduce the length and weight of the grip section of a dental handpiece, and in turn the overall handpiece may be made compact and light. On the other hand, since the power-cord-side connector 5 is arranged offset from the connecting-end opening of the end cap 20 into the interior of the end cap 20, the connector 5 is hard to be touched by the user. Thus, even when the motor unit 11 is detached from the end cap 20 while the connector 5 in the end cap 20 is energized, the risk of the user to accidentally touch the connector 5 is eliminated or at least significantly reduced, to thereby improve safety.

It is also conceivable that the power-cord-side connector 5 is formed as pins which are arranged inside the end cap 20 in the direction of connection of the connectors 5 and 4 (the direction of connection between the end cap 20 and the motor casing 10) and connected to the power cords running through the hose 30, and the motor-unit-side connector 4 as sockets for receiving the pints, which sockets are arranged in the connecting-end opening of the motor casing 10 in the direction of connection of the connectors 4 and 5 (the direction of connection between the motor casing 10 and the end cap 20) and connected to the motor unit 11. This alternative embodiment also provides the same advantage as the embodiment discussed above.

In the joint 1, for guiding connection between the connectors 4 and 5, the guiding projection 71, in this embodiment the guide pin 71, is provided projecting from the connecting-end opening of the motor casing 10, and the guiding recess 72, in this embodiment the guide pit 72, in which the guiding projection 71 is engageable, is provided in the end cap 20. Thus, in joining the motor casing 10 to the end cap 20, the motor-unit-side-connector 4 and the power-cord-side connector 5 may be securely connected inside the end cap 20 simply by aligning the guiding projection 71 with the guide pit 72. It is also conceivable that, for guiding the connection between the connectors 4 and 5, the guiding projection is provided in the end cap 20 and the guiding recess engageable with the guiding projection in the connecting-end opening of the motor casing 10. This alternative embodiment also provides the same advantage as the embodiment discussed above.

According to the present invention, the power cords for the motor along with the water and air tubes for conveying water and air, respectively, and power cords for the light source, extend through the hose 30; the motor unit 11 along with the water and air pipes 61 and 62 for conveying water and air, respectively, and the wiring 631 for supplying power to the light source, are arranged in the motor casing 10; the motor-unit-end connector 4 along with the ends of the water and air pipes 61 and 62, and the power terminal (or power socket) 632 connected to the wiring 631, are arranged in parallel and projecting from the connecting-end opening of the motor casing 10; and corresponding to these, the power-cord-side connector 5 along with the water and air pipe sockets and the power socket (or power terminal) are arranged in parallel and offset from the connecting-end opening of the end cap 20 into the interior of the end cap 20. Thus, by joining the motor casing 10 and the end cap 20, the motor-unit-side connector 4 may be electrically connected to the power-cord-side connector 5 in a secure manner, while the ends of the water and air pipes 61 and 62, and the power terminal 632 may al so be securely connected to the corresponding water and air pipe sockets and the power socket, respectively. Here, the motor-unit-side connector 4, the ends of the water and air pipes 61 and 62, and the power terminal 632 are arranged in circle near and around the center of the connecting-end opening of the motor casing 10 in parallel with each other, whereas the power-cord-side connector 5, the water and air pipe sockets, and the power socket are correspondingly arranged in circle near and around the center of the end cap 20 in parallel with each other. Thus, these parts may be arranged in an area of a minimum diameter in the connecting-end opening of the motor casing 10 and in the end cap 20, and may be connected to the corresponding parts as deep inside the end cap 20 as practicable, for example, in the sensor detectable part.

In the joint 1, by means of the threaded ring 116, the step 116A of a smaller diameter, on which the connecting-end opening of the end cap 20 is capable of fitting, is provided protruding from the connecting-end opening of the motor casing 10, and the male thread 116B is formed circumferentially around the step 116A in its distal part. On the other hand, the female thread 21 is formed circumferentially on the inner surface of the end cap 20 near the connecting-end opening thereof. With these threads 116B and 21, the motor casing 10 is capable of being screwed and integrally joined with the end cap 20. Here, the connecting end of the motor unit 11 is placed inside the end cap 20, and the motor-unit-side connector 4 and the power-cord-side connector 5 are electrically connected inside the end cap 20, while the ends of the water and air pipes 61 and 62, and the power terminal 632 are connected inside the end cap 20 to the corresponding water and air pipe sockets and the power socket, respectively. Thus excellent integral appearance of the motor casing 10 and the end cap 20 may be achieved.

Further, since the joint 1 may have the protection cap 8 which is detachably attachable to the connecting end of the motor unit 11 in place of the end cap 20, the motor-unit-side connector 4 and the various parts 61, 62, 632 projecting from the connecting-end opening may be protected by covering the connecting-end opening with the protection cap 8. If the motor unit 11 detached from the end cap 20 is dropped to the floor or the like, the connector 4 along with the ends of the water and air pipes 61 and 62, and the power terminal 632 of the motor unit 11, which are projected from the connecting-end opening of the motor casing 10, may be broken or damaged. By covering, with the protection cap 8, the connecting-end opening of the motor casing 10 detached from the end cap 20, the connector 4 and the various parts 61, 62, and 632 projecting from the connecting-end opening may be protected. Incidentally, with the motor unit 11 of this embodiment, the guiding projection 71 is projected in the center of the connecting-end opening of the motor casing 10 further beyond the various parts 61, 62, 632. Thus even if the motor casing 10 containing the motor unit 11 without the protection cap 8 is dropped to the floor, the guiding projection 71 is the first to contact the floor, so that unless the guiding projection 71 is bent with a strong impact, damage of the connector 4 and the various parts 61, 62, 632 may be avoided.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A joint for connecting a motor unit to a power cord of a dental handpiece, comprising:
   a generally cylindrical motor casing,
   a motor unit detachably accommodated in said motor casing and supplying driving force to a dental tool,
   a generally cylindrical end cap connected to a hose which accommodates a power cord for supplying power to the motor unit, and detachably connectable to one end of the motor casing, and
   a motor-unit-side connector and a power-cord-side connector arranged between the motor casing and the end cap for mutual electrical engagement,
   said motor casing having an opening at its end to be connected to said end cap, said end cap having an opening at its end to be connected to said motor casing,
   connection of the motor casing to the end cap causing said motor unit to be electrically connected to the power cord, wherein said motor-unit-side connector is connected to the motor unit and arranged projecting outwards from the opening of the motor casing, and said power-cord-side connector is arranged offset from the opening of said end cap into an interior of the end cap,
   wherein said motor casing has a step protruding from the opening of the motor casing, and having a smaller outer diameter sized so that said opening of the end cap is capable of fitting thereon,
   wherein said step has male thread formed on its outer circumference, said thread having a smaller outer diameter than the rest of the motor casing, and said end cap has female thread formed circumferentially on its inner surface near the opening, so that the motor casing is capable of being screwed and fixed to the end cap,
   wherein said male thread is located distal to the motor-unit-side connector, and said female thread is located distal to the power-cord-side connector, and
   wherein said motor-unit-side connector projects beyond the step and the male thread formed on its outer circumference, and said power-cord-side connector is arranged offset beyond the female thread.

2. The joint according to claim 1, wherein one of said motor-unit-side connector and said power-cord-side connector comprises a pin which is connected to the motor unit or the power cord and arranged in the opening of the motor casing or inside the end cap in the direction of connection of the motor-unit-side and power-cord-side connectors, and the other of said motor-unit-side connector and said power-cord-side connector comprises a socket for receiving said pin therein, which socket is connected to the power cord or the motor unit and arranged inside the end cap or in the opening of the motor casing in the direction of connection of the motor-unit-side and power-cord-side connectors.

3. The joint according to claim 1, further comprising a protection cap detachably attachable to the motor casing in place of the end cap for covering the opening of the motor casing to protect the motor-unit-side connector when the end cap is not on the motor casing.

4. The joint according to claim 1, wherein the end cap has a distal end having an outer diameter which is the same as the outer diameter of a proximal end of the motor casing.

5. The joint according to claim 1, wherein said end cap has a proximal end having a smaller outer diameter than the outer diameter at the distal end, and wherein the motor-unit-side connector extends into a smaller outer diameter part of the end cap when the motor-unit-side connector is connected to the power-cord-side connector.

6. The joint according to claim 1, wherein the power cord along with at least one of a fluid tube for conveying fluid and a power cord for supplying power to a light source extend through the hose, the motor unit along with at least one of a pipe for conveying said fluid and wiring for supplying said power to the light source are accommodated in the motor casing, the motor-unit-side connector along with at least one of an end of said pipe and a power terminal or socket connected to the wiring are projected from the opening of the motor casing in parallel with each other, and the power-cord-side connector along with at least one of a pipe socket and a power socket or power terminal connected to the pipe for conveying said fluid or the power terminal or the power socket are arranged offset from the opening of the end cap into the interior of the end cap in parallel with each other.

7. The joint according to claim 6, wherein the motor-unit-side connector and at least one of said end of the pipe and said power terminal or socket are arranged in circle near and around a center of the opening of the motor casing in parallel with each other, and the power-cord-side connector and at least one of said pipe socket and said power socket or terminal are arranged in circle near and around a center of the end cap in parallel with each other.

8. The joint according to claim 1, further comprising a guiding projection and a guiding recess capable of receiving the guiding projection therein for guiding connection of the motor-unit-side connector to the power-cord-side connector.

9. The joint according to claim 8, wherein said guiding projection is a guide pin projecting from and in the center of the opening of the motor casing in a direction of connection of the motor-unit-side and power-cord-side connectors outwardly beyond the motor-unit-side connector, and
   wherein said guiding recess is a guide pit extending inside and in the center of the opening of the end cap in the direction of connection of the motor-unit-side and power-cord-side connectors, so that the guide pin is insertable into the guide pit.

10. The joint according to claim 9, wherein the end cap has a proximal end having a smaller outer diameter than the outer diameter at the distal end, and has a contour tapered from the distal end to the proximal end, and wherein the guide pit extends substantially into an area of the end cap having a diameter substantially less than the diameter of the end cap at the distal end.

* * * * *